United States Patent [19]

Acier et al.

[11] Patent Number: 5,311,225
[45] Date of Patent: May 10, 1994

[54] DEVICE FOR DETERMINING THE PORTION OF A FIELD SEEN BY THE EYE OF AN OBSERVER

[75] Inventors: Bruno Acier, Chartres; Jean-Pierre Merle, Orsay; Jacques R. Des Ordons, Savigny Sur Orge, all of France

[73] Assignee: Societe Anonyme dite: Aerospatiale Societe Nationale Industrielle, Paris, France

[21] Appl. No.: 983,504

[22] Filed: Nov. 30, 1992

[30] Foreign Application Priority Data

Dec. 13, 1991 [FR] France .................. 91 15509

[51] Int. Cl.[5] .............................. G02C 5/14
[52] U.S. Cl. .............................. 351/221; 351/211; 351/205; 351/206; 351/201; 351/209
[58] Field of Search ............ 351/221, 211, 205, 206, 351/201, 209

[56] References Cited

U.S. PATENT DOCUMENTS

| 4,852,988 | 8/1989 | Velez et al. ............... 351/210 |
| 5,152,295 | 10/1992 | Kobayashi ............... 351/206 |

FOREIGN PATENT DOCUMENTS 0434289  6/1991  European Pat. Off. .
2522804  9/1983  France .
2561371  9/1985  France .

OTHER PUBLICATIONS

Patent Abstracts of Japan, vol. 15, No. 305, Aug. 5, 1991.

Primary Examiner—Loha Ben
Assistant Examiner—Thomas Robbins
Attorney, Agent, or Firm—Marshall, O'Toole, Gerstein, Murray & Borun

[57] ABSTRACT

Device intended to determine the portion of a field seen by the eye (5) of an observer.

According to the invention, this device includes:
- an optical sighting system (2, 3) through which said eye (5) looks at said field, said optical system comprising an exit eyepiece (15) behind which said eye (5) is placed; and
- a first optical component (22) placed on the side of the object focal plane of said exit eyepiece (15), said first optical component letting through the light rays (16) which come from said field and which pass through said optical sighting system and sending to said eye (5) a light beam (24) emitted by a light source (23) in order to form at least one reflection.

13 Claims, 2 Drawing Sheets

DEVICE FOR DETERMINING THE PORTION OF A FIELD SEEN BY THE EYE OF AN OBSERVER

The present invention concerns a device for determining the portion of a field seen by the eye of an observer, such a device generally being called an "oculometer" in the art.

There is known already, for example through the Patent EP-A-0 157 973, a device intended to determine the portion of a field seen by the eye of an observer and comprising:

- a light source sending a light beam on to the cornea of said eye in order to form a corneal reflection;
- a first image detector observing said corneal reflection and generating first electrical signals representative of the orientation of the optic axis of said eye;
- a second image detector observing said field and generating second electrical signals representative of said field; and
- computing means receiving said first and second electrical signals and delivering third electrical signals representative of the portion of said field seen by said eye.

The functioning of such a device is based mainly on the information contained in the publication of Mackworth et al, "Eye Fixations Recorded on Changing Visual Scenes by the Television Eye Marker" in *Journal of the Optical Society of America*, July 1958 and showing that there is a correlation between the variation in the orientation of the optic axis of the eye and the displacement of said corneal reflection.

Consequently, by observing said corneal reflection, said first image detector knows, at each instant, the position of the corneal reflection and the orientation of the optic axis of the eye. Said computing means can thus determine the portion of the field seen at each instant by said eye, since it receives the information about the field coming from the second image detector.

Said first and second image detectors may be of the camera type, for example of the CCD type and, preferably, said light source is invisible (infra-red) in order not to bother the observer. It is generally of the LED diode type.

According to a known variant of implementation, it is possible to combine with said corneal reflection the retinal reflection generated by said light beam and stopped down by the pupil, in order to determine the orientation of the optic axis of the eye.

In the known devices of the type described above, the eye of the observer looks at the field directly, without the interposition of an optical system, such as a sighting telescope, limiting the peripheral vision. There is thus no obstacle to the illumination of the eye by the source of invisible light.

On the other hand, if it is desired to provide an optical system for the observation of the field by the eye of the observer, difficulties are encountered.

In effect, the eye has to be located near to the eyepiece of the optical system, in the plane of the pupil of said optical system. Consequently, it is impossible, through lack of space, to introduce the invisible light beam between the eyepiece of the optical system and the eye. In addition, if it were envisaged that the eye was to be illuminated by invisible light through said optical system, the beam of invisible light would be limited in diameter by the pupil of said optical system. Given that the area of the pupil of an optical system is small in comparison with the area of the cornea to be illuminated, this would make it impossible to illuminate the whole cornea and thus to measure all the orientations of the optic axis of the eye.

The aim of the present invention is to overcome these disadvantages and to make it possible to provide the devices of the type described above with an optical system.

To this end, according to the invention, the device intended to determine the portion of a field seen by the eye of an observer and comprising:

- a light source sending a light beam on to said eye in order to form at least one reflection;
- a first image detector observing said reflection and generating first electrical signals representative of the orientation of the optic axis of said eye;
- a second image detector observing said field and generating second electrical signals representative of said field; and
- computing means receiving said first and second electrical signals and delivering third electrical signals representative of the portion of said field seen by said eye;

is noteworthy in that it comprises:

- an optical sighting system through which said eye looks at said field, said optical system comprising an exit eyepiece behind which said eye is placed; and
- a first optical component placed on the side of the object focal plane of said exit eyepiece, said first optical component letting through the light rays which come from said field and which pass through said optical system and sending to said eye said light beam emitted by said light source.

Thus, said light beam, intended to illuminate the eye, passes through said exit eyepiece. The latter therefore has a dual role, i.e. (i) to send the image of the field to the eye through the exit pupil of the optical sighting system and (ii) to illuminate said eye with the light emitted by said source, without limitation by said exit pupil.

Preferably, particularly when the device is intended for the determination of the portion of the field seen by the eye by the known method using, apart from said corneal reflection, the retinal reflection generated by said light beam (called the "corneal vector" method), said first optical component is placed in the object focal plane of said exit eyepiece.

According to a first mode of embodiment, said first optical component, which may be of the type consisting of a parallel plate with treated surfaces, is, on one side, at least partially transparent for the light rays coming from said field and, on the other side, partially transparent and partially reflecting for said light beam emitted by said light source.

Consequently, the part of said light beam reflected by the eye may pass through said first optical component and be directed towards a second optical component, coupled optically to said first and second image detectors and placed upstream (with respect to the direction of propagation of the light rays coming from said field) of said first optical component, said second optical component being, on one side, partially transparent and partially reflecting for the light rays coming from said field and, on the other side, at least partially reflecting for said light beam emitted by said light source.

In this case, it is an advantage for said optical sighting system to include an afocal optical vehicle defining an intermediate point of convergence, at the site of which said second optical component is placed.

The optical sighting system can then include a sighting telescope, of the astronomical telescope type, to which said optical vehicle is firmly attached, the latter comprising an objective coupled optically to the eyepiece of said sighting telescope and an eyepiece forming said exit eyepiece of said optical system.

It will be noted that this mode of embodiment is particularly advantageous since it enables said sighting telescope to be adapted, without modifying it, for use in the device in accordance with the present invention. A sensor is thus obtained which is intended to be coupled to an ordinary sighting telescope in order to make it suitable for the device of the invention.

Thus, the present invention also concerns a sensor intended to form, with a sighting telescope, an optical sighting system for a device intended to determine the portion of a field seen by the eye of an observer, the device comprising:
  a light source sending a light beam on to said eye in order to form at least one reflection;
  a first image detector observing said reflection and generating first electrical signals representative of the orientation of the optic axis of said eye;
  a second image detector observing said field and generating second electrical signals representative of said field; and
  computing means receiving said first and second electrical signals and delivering third electrical signals representative of the portion of said field seen by said eye.

According to the present invention, such a sensor is noteworthy in that it includes:
  an afocal optical vehicle attached firmly to said sighting telescope, said optical vehicle comprising an objective coupled to the eyepiece of said sighting telescope and an eyepiece forming the exit eyepiece of said optical system;
  a first optical component placed on the side of the object focal plane of said exit eyepiece and sending to said eye said light beam emitted by said light source, said first optical component being, on one side, at least partially transparent for the light rays coming from said field and, on the other side, partially transparent and partially reflecting for said light beam emitted by said light source; and
  a second optical component coupled optically to said first and second image detectors and placed between said objective and said first optical component, said second optical component being, on one side, partially transparent and partially reflecting for the light rays coming from said field and, on the other side, at least partially reflecting for said light beam emitted by said light source.

Preferably, in order to form a constructional entity, said light source and/or said first and second image detectors are incorporated in said sensor.

According to a second mode of embodiment, said first optical component, which may also be of the type consisting of a parallel plate with treated surfaces, is, on one side, partially transparent and partially reflecting for the light rays coming from said field and, on the other side, at least partially reflecting for said light beam emitted by said light source.

Thus, said first optical component may be coupled optically to said first and second image detectors, the coupling with said first image detector being obtained by using a third optical component, on one side at least partially transparent and on the other side at least partially reflecting for said light beam emitted by said light source and making it possible to separate from this beam the part which is reflected by the eye and by said first optical component.

In this case, it is an advantage for said first and third optical components to be incorporated in a sighting telescope in order to form said optical system, the eyepiece of said sighting telescope forming the exit eyepiece of said optical system.

An optical system intended quite specifically for the device in accordance with the present invention is then obtained by modification of an ordinary sighting telescope.

Thus, the present invention also concerns an optical sighting system for a device intended to determine the portion of a field seen by the eye of an observer, said device comprising:
  a light source sending a light beam on to said eye in order to form at least one reflection;
  a first image detector observing said reflection and generating first electrical signals representative of the orientation of the optic axis of said eye;
  a second image detector observing said field and generating second electrical signals representative of said field; and
  computing means receiving said first and second electrical signals and delivering third electrical signals representative of the portion of said field seen by said eye;
said optical system being noteworthy in that it includes:
  a sighting telescope provided with an eyepiece;
  a first optical component placed on the side of the object focal plane of said eyepiece of the sighting telescope and sending to said eye said light beam emitted by said light source, said first optical component being, on one side, partially transparent and partially reflecting for the light rays coming from said field and, on the other side, at least partially reflecting for said light beam emitted by said light source, said first optical component being optically coupled to said second image detector; and
  a third optical component, on one side at least partially transparent and on the other side at least partially reflecting for said light beam emitted by said light source, said third optical component providing for the separation between said light beam and that part of it reflected by the eye and said first optical component, and for the optical coupling between said first optical component and said first image detector.

Preferably, in order to form a single assembly, said light source and/or said first and second image detectors are incorporated in said optical system.

The figures in the appended drawing will make it easy to understand how the invention may be produced. In these figures, the same reference numbers indicate similar components.

Figure 1:
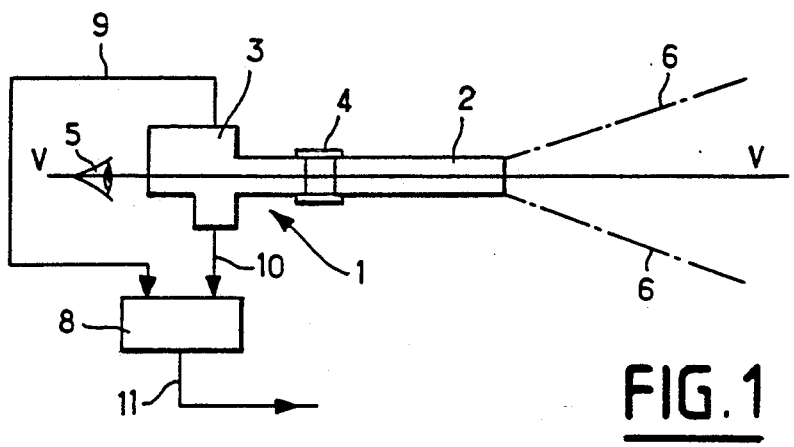
FIG. 1 shows diagrammatically a first mode of embodiment of the device in accordance with the present invention.

The device 1, in accordance with the present invention and represented diagrammatically in FIG. 1, comprises a sighting telescope 2, for example of the astronomical telescope type, and an optical-electrical sensor 3, attached firmly to each other by a fixing member 4, in such a way that their optic axes are strictly aligned along a common optic axis defining a line of sight V—V.

Figure 2:
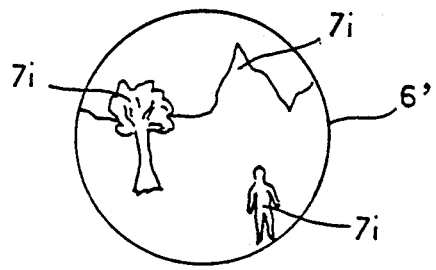
FIG. 2 shows diagrammatically the image of a field seen through the device of the invention.

An eye 5 of an observer is placed on the line of sight V—V, behind the sensor 3, so that it can look at the field 6 defined by the sighting telescope 2. As is illustrated in FIG. 2, the eye 5 therefore sees the image 6' of the field 6 through the telescope 2 and the sensor 3, as well as the images of the different elements or portions 7i making up this field.

Moreover, the device 1 of FIG. 1 includes a computer 8 receiving the output electrical signals 9 and 10 from the sensor 3 and processing them in order to deliver signals to its output 11.

Figure 3:
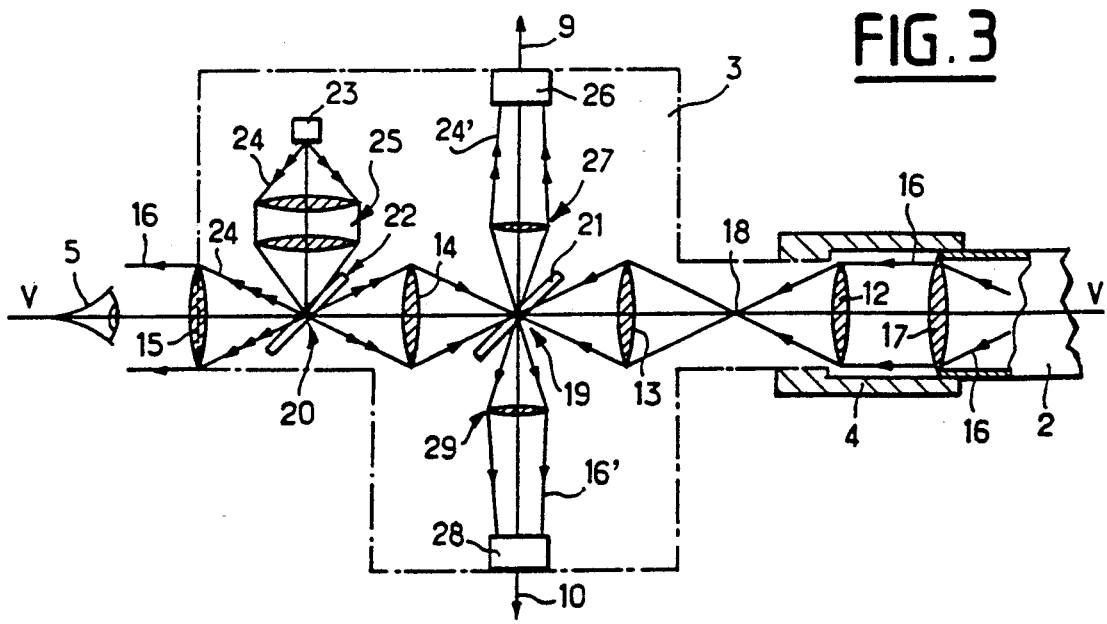
FIG. 3 is a partial view, enlarged and shown in cross-section, of the device of FIG. 1.

As is shown diagrammatically in FIG. 3, in which the telescope 2 is represented only partially, the optical-electrical sensor 3 comprises a set of four converging lenses 12, 13, 14 and 15, centered on the line of sight V—V and placed along it in such a way as to form an afocal and achromatic optical vehicle.

The lens 12 acts as an objective for the sensor 3 and it receives from the eyepiece 17 of the sighting telescope 2 the beam 16, passing through said sighting telescope 2 and then consisting of parallel rays as a result of its passage through said eyepiece 17. It makes it converge to its image focus 18. Each of the lenses 13 and 14 cause the beam 16 to converge again, to the intermediate points 19 and 20 respectively. The point 20 coincides with the object focus of the lens 15. Thus, the lens 15 acts as an exit eyepiece for the assembly consisting of the sighting telescope 2 and the sensor 3 and sends to the eye 5 the beam 16, once again in the form of parallel rays. The eye 5 therefore sees the image 6' after inversion by the lens 12, rectification by the lens 13, inversion by the lens 14 and rectification by the exit eyepiece 15.

At the point of convergence 19, between the lenses 13 and 14, is placed an inclined plate 21, which, on one side, is semi-transparent and semi-reflecting for the beam 16 and, on the other, is at least partially reflecting for the infrared light.

Furthermore, at the object focus 20 of the exit eyepiece 15 is placed an inclined plate 22, which, on one side, is transparent for the beam 16 and, on the other, is semi-reflecting and semi-transparent for the infrared light.

Moreover, the sensor 3 comprises:
a source of infrared light 23, for example an LED diode emitting an infrared beam 24 which, through the action of an optical system 25, is made to converge on to the inclined plate 22;
an infrared CCD camera 26, placed opposite the inclined plate 21, with the interposition of an optical system 27, the output from the camera 26 forming the output 9 from the sensor 3; and
a CCD camera 28, placed opposite the inclined plate 21, with the interposition of an optical system 29, the output from the camera 28 forming the output 10 from the sensor 3.

Thus, the beam 16 coming from the eyepiece 17 of the sighting telescope 2 is sent to the eye 5 through the lenses 12 to 15 in the way indicated above, by passing through the inclined plates 21 and 22. In addition, a part 16' of the beam 16 is sent to the camera 28 by reflection on the inclined plate 21 and through the optical system 29. The electrical signals appearing at the output 10 therefore represent the image 6' of the field 6.

For its part, the beam 24 is sent to the eye 5 in the form of a beam of parallel rays, by virtue of reflection on the plate 22 and of the action of the exit eyepiece 15. This beam 24 therefore generates, by illumination of the cornea and the retina of the eye 5 and by reflection on them, a corneal reflection and a retinal reflection conveyed by a beam 24', which, in the opposite direction to the beam 16, passes through the exit eyepiece 15, the inclined plate 20 and the lens 14, in order to be reflected on the inclined plate 21 before being sent to the camera 26 through the optical system 27.

Since the difference in position between this corneal reflection and the center of the bright pupil formed by the retinal reflection is representative of the orientation of the optic axis of the eye 5, the information supplied at the output 9 of the camera 26 is representative of that element 7i of the image 6' which is seen by said eye 5.

Consequently, the computer 8, receiving at its inputs the electrical signals coming from the outputs 9 and 10 of the cameras 26 and 28, is capable of delivering at its output 11, by a known processing of said electrical input signals, output electrical signals representative of said element 7i seen by the eye 5.

Figure 4:
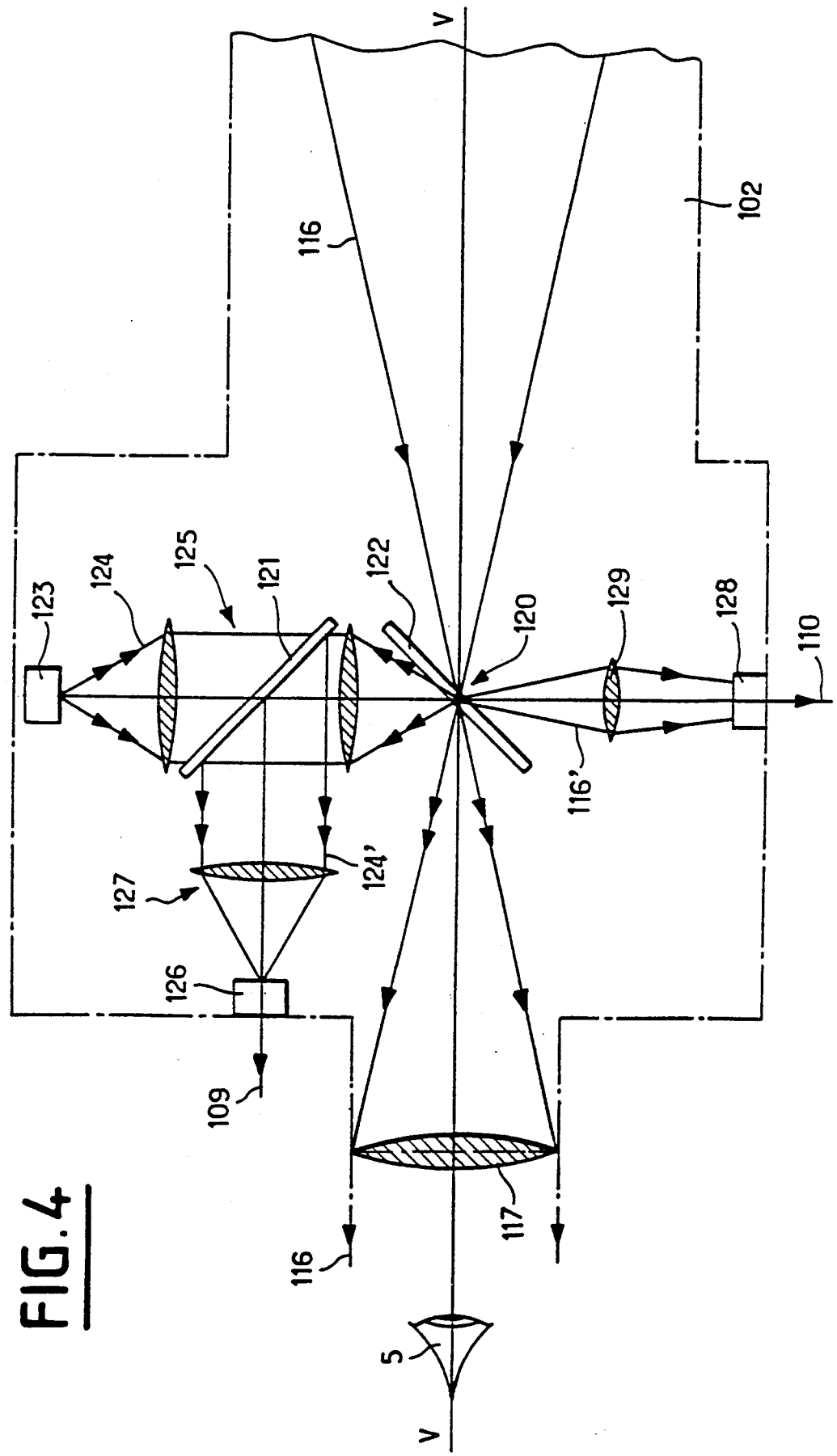
FIG. 4 illustrates, in partial cross-section, a second mode of embodiment of the device in accordance with the present invention.

FIG. 4 is a partial representation of a sighting telescope 102, improved according to the invention and intended to replace, in the device 1 of FIG. 1, the assembly consisting of the ordinary sighting telescope 2 and the sensor 3. The optic axis, or line of sight, of the telescope 102 also carries the reference V—V.

The telescope 102 includes an eyepiece 117 and the eye 5 is placed behind this eyepiece in order to receive the optical beam 116 passing through said telescope (coming from the objective, not represented, of said telescope 102) and in order to see the image 6' (FIG. 2) of the field 6. The telescope 102 includes outputs 109 and 110, respectively analogous to the outputs 9 and 10 described above.

At the object focus 120 of the eyepiece 117 is placed an inclined plate 122 which, on one side, is partially transparent and partially reflecting for the beam 116 and, on the other side, at least partially reflecting for the infrared light.

Moreover, the telescope 102 comprises:
a source of infrared light 123 (LED diode), emitting an infrared beam 124 which, by the action of an optical system 125, is made to converge on to the inclined plate 122;
an inclined plate 121, placed in the path of the beam 124, said plate 121 being, on one side, at least partially transparent and, on the other, at least partially reflecting for the infrared light;
an infrared CCD camera 126, placed opposite the inclined plate 121, with the interposition of an optical system 127, the output from the camera 126 forming the output 109 from the telescope 102; and
a CCD camera 128, placed opposite the inclined plate 122, with the interposition of an optical system 129, the output from the camera 128 forming the output 110 from the telescope 102.

Thus, the beam 116 passing through the sighting telescope 102 is sent to the eye 5 through the inclined plate 122 and the eyepiece 117. Moreover, a part 116' of the beam 116 is sent to the camera 128 by reflection on the inclined plate 122 and through the optical system 129. The electrical signals appear at the output 110, therefore representing the image 6' of the field 6.

The infrared beam 124 is sent to the eye 5 in the form of a parallel beam, after having passed through the, inclined plate 121 and the optical system 125, by virtue of reflection on the inclined plate 122 and of the action of the eyepiece 117 of the telescope 102. This beam 124 thus generates, by illumination of the cornea and retina of the eye 5 and by reflection on them, a corneal reflection and a retinal reflection conveyed by a beam 124', which, in the opposite direction to the beam 116, passes through the eyepiece 117 and is reflected on the inclined plates 122 and 121, before being sent to the camera 126 through the optical system 127.

It can therefore be seen that, on the outputs 109 and 110, there appear electrical signals similar respectively to those appearing on the outputs 9 and 10 mentioned above. Consequently, the computer 8 can, in the same way, process the signals from said outputs 109 and 110, in order to deliver to its output 11 electrical signals representative of the element 7i seen by the eye 5 through the telescope 102.

From the above description, it will be noticed that, by virtue of the invention, it is easy to produce a binocular device by combining an optical system 2, 3 or 102 with each of the two eyes 5 of an observer. In this case, it is an advantage for the computer 8 to process the signals coming from the two optical systems 2, 3 or 102.

We claim:

1. A device (1) intended to determine the portion (7i) of a field (6) seen by the eye (5) of an observer and comprising:
    a light source (23; 123) sending a light beam (24; 124) on to said eye (5) in order to form at least one reflection;
    a first image detector (26; 126) observing said reflection and generating first electrical signals representative of the orientation of the optic axis of said eye (5);
    a second image detector (28; 128) observing said field (6) and generating second electrical signals representative of said field (6); and
    computing means (8) receiving said first and second electrical signals and delivering third electrical signals representative of the portion (7i) of said field (6) seen by said eye (5);
    an optical sighting system (2, 3; 102) through which said eye (5) looks at said field (6), said optical system comprising an exit eyepiece (15; 117) behind which said eye (5) is placed; and
    a first optical component (22; 122) placed on the side of the object focal plane of said exit eyepiece (15, 117), said first optical component letting through the light rays (16, 116) which come from said field (6) and which pass through said optical sighting system and sending to said eye (5) said light beam (24; 124) emitted by said light source (23; 123).

2. The device as claimed in claim 1, characterized in that said first optical component (22; 122) is placed in the object focal plane of said exit eyepiece (15; 117).

3. The device as claimed in claim 1, characterized in that said first optical component (22) is, on one side, at least partially transparent for the light rays (16) coming from said field (6) and, on the other side, partially transparent and partially reflecting for said light beam (24) emitted by said light source (23).

4. The device as claimed in claim 3, characterized in that the part (24') of said light beam (24) reflected by the eye passes through said first optical component (22) and is directed towards a second optical component (21), coupled optically to said first and second image detectors (26, 28) and placed upstream (with respect to the direction of propagation of the light rays (16) coming from said field) of said first optical component (22), said second optical component (21) being, on one side, partially transparent and partially reflecting for the light rays (16) coming from said field (6) and, on the other side, at least partially reflecting for said light beam (24) emitted by said light source.

5. The device as claimed in claim 4, characterized in that said optical sighting system includes an afocal optical vehicle (12 to 15) defining an intermediate point of convergence (19), at the site of which said second optical component (21) is placed.

6. The device as claimed in claim 5, characterized in that the optical sighting system includes a sighting telescope (2), to which said optical vehicle (12 to 15) is firmly attached, the latter comprising an objective (12) coupled optically to the eyepiece (17) of said sighting telescope (2) and an eyepiece (15) forming said exit eyepiece of said optical system.

7. The device as claimed in claim 1, characterized in that said first optical component (122) is, on one side, partially transparent and partially reflecting for the light rays (116) coming from said field (6) and, on the other side, at least partially reflecting for said light beam (124) emitted by said light source (123).

8. The device as claimed in claim 7, characterized in that said first optical component (122) is coupled optically to said first and second image detectors (126, 128), the coupling with said first image detector (126) being obtained by using a third optical component (121), on one side at least partially transparent and, on the other side, at least partially reflecting for said light beam (124) emitted by said light source (123) and making it possible to separate from this beam (124) the part (124') which is reflected by the eye and by said first optical component (122).

9. The device as claimed in claim 8, characterized in that said first and third optical components (122, 121) are incorporated in a sighting telescope in order to form said optical system (102), the eyepiece (117) of said sighting telescope forming the exit eyepiece of said optical system.

10. A sensor (3) forming, with a sighting telescope (2), an optical sighting system for a device intended to determine the portion (7i) of a field (6) seen by the eye (5) of an observer, the device comprising:
    a light source (23) sending a light beam (24) on to said eye (5) in order to form a reflection;
    a first image detector (26) observing said reflection and generating first electrical signals representative of the orientation of the optic axis of said eye (5);
    a second image detector (28) observing said field (6) and generating second electrical signals representative of said field; and
    computing means (8) receiving said first and second electrical signals and delivering third electrical signals representative of the portion (7i) of said field (6) seen by said eye (5);
    an afocal optical vehicle (12 to 15) attached firmly to said sighting telescope (2), said optical vehicle comprising an objective (12) coupled to the eyepiece (17) of said sighting telescope and an eyepiece (15) forming the exit eyepiece of said optical system;

a first optical component (22) placed on the side of the object focal plane of said exit eyepiece (15) and sending to said eye (5) said light beam (24) emitted by said light source (23), said first optical component (22) being, on one side, at least partially transparent for the light rays (16) coming from said field and, on the other side, partially transparent and partially reflecting for said light beam (24) emitted by said light source (23); and a second optical component (21) coupled optically to said first and second image detectors (26, 28) and placed between said objective (12) and said first optical component (22), said second optical component (21) being, on one side, partially transparent and partially reflecting for the light rays (16) coming from said field and, on the other side, at least partially reflecting for said light beam (24) emitted by said light source (23).

11. The sensor as claimed in claim 10, characterized in that said first optical component (22) is placed in the object focal plane of said exit eyepiece (15).

12. An optical sighting system for a device intended to determine the portion (7i) of a field (6) seen by the eye (5) of an observer, said device comprising:

a light source (123) sending a light beam (124) on to said eye (5) in order to form a reflection;

a first image detector (126) observing said reflection and generating first electrical signals representative of the orientation of the optic axis of said eye (5);

a second image detector (128) observing said field (6) and generating second electrical signals representative of said field; and computing means (8) receiving said first and second electrical signals and delivering third electrical signals representative of the portion (7i) of said field (6) seen by said eye (5);

a sighting telescope (102) provided with an eyepiece (117);

a first optical component (122) placed on the side of the object focal plane of said eyepiece (117) of the sighting telescope (102) and sending to said eye (5) said light beam (124) emitted by said light source (123), said first optical component (122) being, on one side, partially transparent and partially reflecting for the light rays (116) coming from said field (6) and, on the other side, at least partially reflecting for said light beam (124) emitted by said light source (123), said first optical component (122) being optically coupled to said second image detector (128); and a third optical component (121), on one side at least partially transparent and on the other side partially reflecting for said light beam (124) emitted by said light source (123), said third optical component (121) providing for the separation between said light beam (124) and that part of it (124') reflected by said eye and said first optical component (122), and for the optical coupling between said first optical component (122) and said first image detector (126).

13. The optical system as claimed in claim 12, characterized in that said first optical component (122) is placed in the object focal plane of said eyepiece (117).

* * * * *